United States Patent [19]

Bühler et al.

[11] Patent Number: 5,672,317
[45] Date of Patent: Sep. 30, 1997

[54] ANALYZER WITH FIXED POSITION BAR CODE READER

[75] Inventors: Jürg Bühler, Rothenburg; Siegfried Müller, Meierskappel, both of Switzerland

[73] Assignee: Roche Diagnostics Systems, Inc., Branchburg, N.J.

[21] Appl. No.: 624,854

[22] Filed: Mar. 22, 1996

[30] Foreign Application Priority Data

Apr. 19, 1995 [CH] Switzerland ............... 1119/95

[51] Int. Cl.$^6$ ..................................... G01N 35/02
[52] U.S. Cl. ................. 422/65; 422/63; 422/67; 436/43; 436/47; 436/48; 436/50; 356/244; 356/246; 235/385; 206/459.5; 211/74
[58] Field of Search .................. 422/63, 65, 66, 422/67, 102, 104, 119; 436/43, 47, 48, 50, 183, 809; 356/246, 244; 235/454, 462, 486, 385; 141/130; 206/443, 446, 485, 459.5; 211/74, 60.1

[56] References Cited

U.S. PATENT DOCUMENTS

| 3,233,804 | 2/1966 | Dahm. | |
|---|---|---|---|
| 3,713,771 | 1/1973 | Taylor et al. | 436/48 |
| 3,897,216 | 7/1975 | Jones | 422/104 |
| 3,916,157 | 10/1975 | Roulette et al. | 235/449 |
| 4,534,465 | 8/1985 | Rothermel et al. | 206/443 |
| 4,877,134 | 10/1989 | Klein. | |
| 4,920,255 | 4/1990 | Gabeler. | |
| 5,128,105 | 7/1992 | Berthold et al. | 422/104 |
| 5,137,693 | 8/1992 | Mawhirt | 422/104 |
| 5,186,339 | 2/1993 | Heisller | 211/74 |
| 5,350,564 | 9/1994 | Mazza et al. | 422/63 |
| 5,378,433 | 1/1995 | Duckett et al. | 422/100 |
| 5,397,542 | 3/1995 | Nelms et al. | 422/104 |
| 5,427,743 | 6/1995 | Markin | 422/104 |
| 5,582,795 | 12/1996 | Nishina et al. | 422/65 |

FOREIGN PATENT DOCUMENTS

| 356250 | 2/1990 | European Pat. Off. |
| 4 142 701 | 7/1993 | Germany. |
| 83/00393 | 2/1983 | WIPO. |
| 94/19698 | 9/1994 | WIPO. |

*Primary Examiner*—Long V. Le
*Attorney, Agent, or Firm*—George W. Johnston; William H. Epstein; John P. Parise

[57] ABSTRACT

An analyzer automatically performs analytical operations in which liquid samples for analysis and required reagents are held in suitable vessels. To increase the number of vessels which can be received in the analyzer and to simplify the device for reading the bar code labels, the analyzer contains at least two vessel holders, a bar code reader, and means for automatically adjusting the focal range and the bar code reader. The vessel holders are disposed parallel to one another in the analyzer. A number of vessels of the same kind (for example, sample-containing vessels) are disposed in each vessel holder. Each vessel holder has an elongate body manufactured in one piece and contains a single straight row of identical elongate chambers for receiving one vessel. All chambers have a common base and are disposed perpendicularly thereto. Adjacent chambers are separated by a partition. The inner surface of a side wall of each chamber bears a first bar code label for detecting the absence of a vessel in the chamber. The outer surface of a side wall of each chamber bears a second bar code label for detecting the position of the chamber in the vessel holder. The first and the second bar code labels are readable by a bar code reader from one and the same side of the vessel holder. The bar code reader is fixedly disposed in the analyzer and used to read all the bar code labels on each vessel holder. The means for automatically adjusting the focal range of the bar code reader is dependent on the distance between it and the vessel holder.

6 Claims, 14 Drawing Sheets

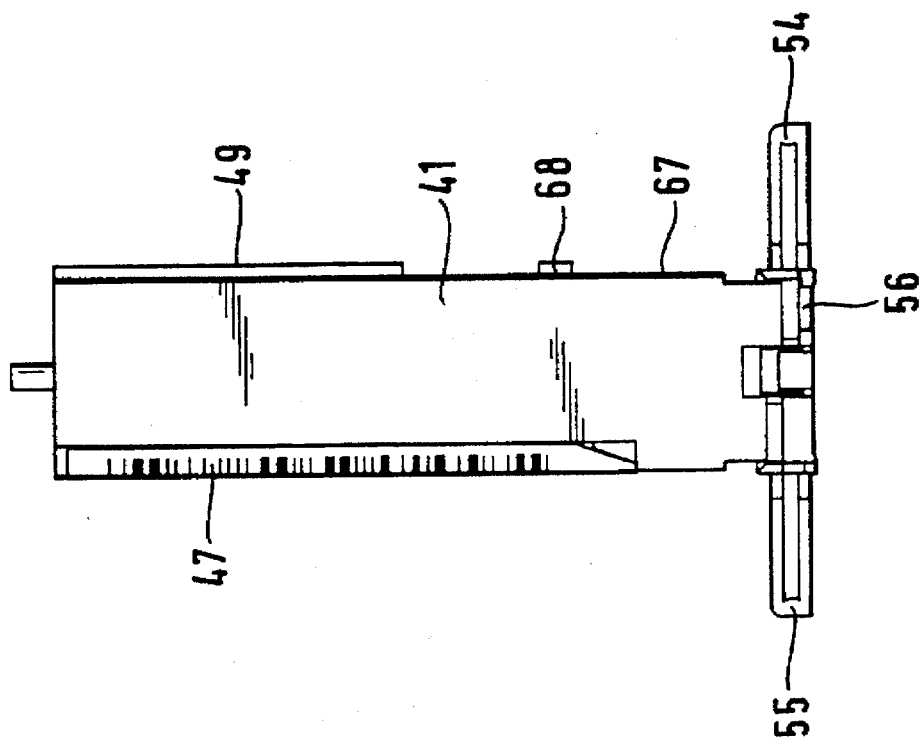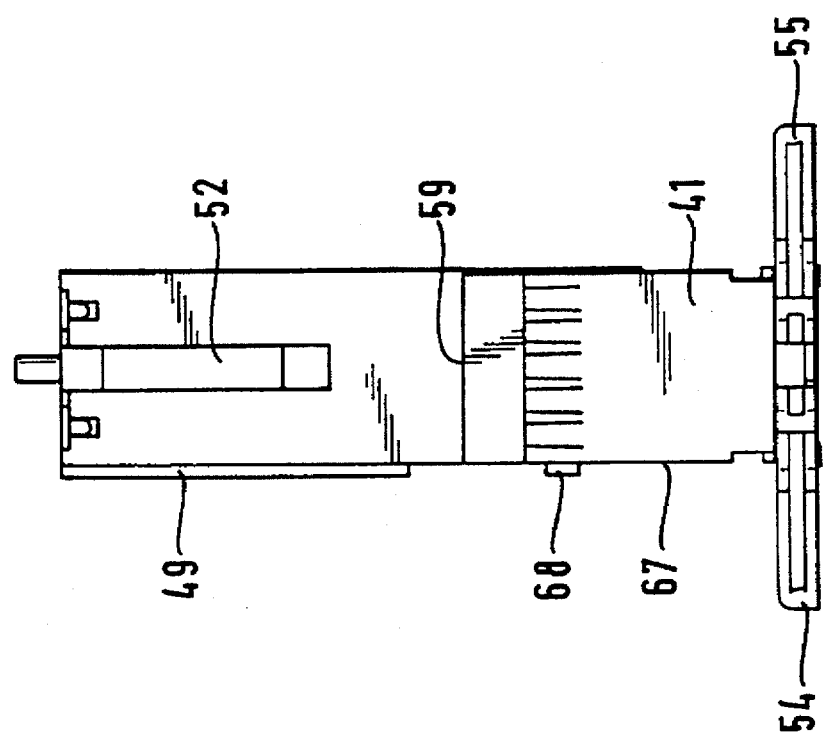

5,672,317

ANALYZER WITH FIXED POSITION BAR CODE READER

BACKGROUND OF THE INVENTION

1. Field

The invention relates to an analyzer for automatically performing analytical operations in which liquid samples to be analyzed and required reagents are contained in suitable vessels.

2. Description

In modern analyzers it is desirable for sample vessels and reagent vessels to be disposed very close to one another. Such dense packing of vessels minimizes the size of the analyzer, and promotes efficiencies. Known analyzers achieve this object to only a limited extent. This is because a space is required for a conveyor that conveys a bar code reader between the rows of vessels. This conveyor positions the bar code reader near the individual vessels so that it can read the bar code labels on the vessels. Unfortunately, such a physical conveyance of the bar code reader increases the mechanical complexity of the analyzer.

Therefore, an object of the invention is to provide an analyzer in which a greater number of vessels can be disposed in the available space and the bar code labels can be read by a much simpler device.

SUMMARY OF THE INVENTION

The present invention provides an analyzer for automatically performing analytical operations using liquid samples and reagents that are contained in vessels. The analyzer comprises at least two vessel holders, a bar code reader, and means for automatically adjusting the focal range of the bar code reader.

At least two vessel holders are disposed parallel to one another during operation of the analyzer. Each vessel holder is configured and dimensioned to hold a plurality of vessels and contains a single straight row of parallelly oriented elongate chambers. Each chamber is configured and dimensioned for receiving one vessel. Adjacent chambers are separated by a partition. Each chamber has a first side wall and a second side wall. Each side wall has an inner surface and an outer surface. The inner surface of the first side wall of each chamber bears a first bar code label for detecting the absence of a vessel in the chamber. The outer surface of the second side wall of each chamber bears a second bar code label for detecting the position of the chamber in the vessel holder. The first bar code label and the second bar code label is readable from the same side of the vessel holder. The bar code reader has a focal range, is fixedly disposed in the analyzer, and is positioned to read all of the bar code labels on each vessel holder as the vessel holder is inserted into the analyzer. Means for automatically adjusting the focal range of the bar code reader are dependent on the distance between the bar code reader and the vessel holder.

BRIEF DESCRIPTION OF THE FIGURES

An exemplified embodiment of the invention will now be described with reference to the accompanying drawings in which:

FIG. 14 is a left-side view of the vessel holder in FIG. 3;

FIG. 15 is a right-side view of the vessel holder in FIG. 3 and

DETAILED DESCRIPTION OF THE INVENTION

The subject invention will now be described in terms of its preferred embodiments. These embodiments are set forth to aid in understanding the invention, but are not to be construed as limiting.

According to the invention, the above described problems are solved by an analyzer which contains the following components:

a) at least two vessel holders disposed parallel to one another in the analyzer, a number of vessels of the same kind (e.g. sample-containing vessels) being disposed in each vessel holder, each vessel holder having an elongate body manufactured in one piece and containing a single straight row of identical elongate chambers each for receiving one vessel, all the chambers having a common base and being disposed perpendicularly thereto, adjacent chambers being separated by a partition, the inner surface of a side wall of each chamber bearing a first bar code label for detecting the absence of a vessel in the chamber, the outer surface of a side wall of each chamber bearing a second bar code label for detecting the position of the chamber in the vessel holder, and the first and the second bar code labels being readable by a bar code reader from one and the same side of the vessel holder, b) a bar code reader fixedly disposed in the analyzer and used to read all the bar code labels on each vessel holder, and c) means for automatically adjusting the focal range of the bar code reader in dependence on the distance between it and the vessel holder.

The main advantage of the analyzer according to the invention is that the vessels in the analyzer can be disposed very close to one another, because no space between the rows of vessels is needed for reading by the bar code reader. Another advantage of using a fixed bar code reader is that no means are necessary for conveying it.

Figure 1:
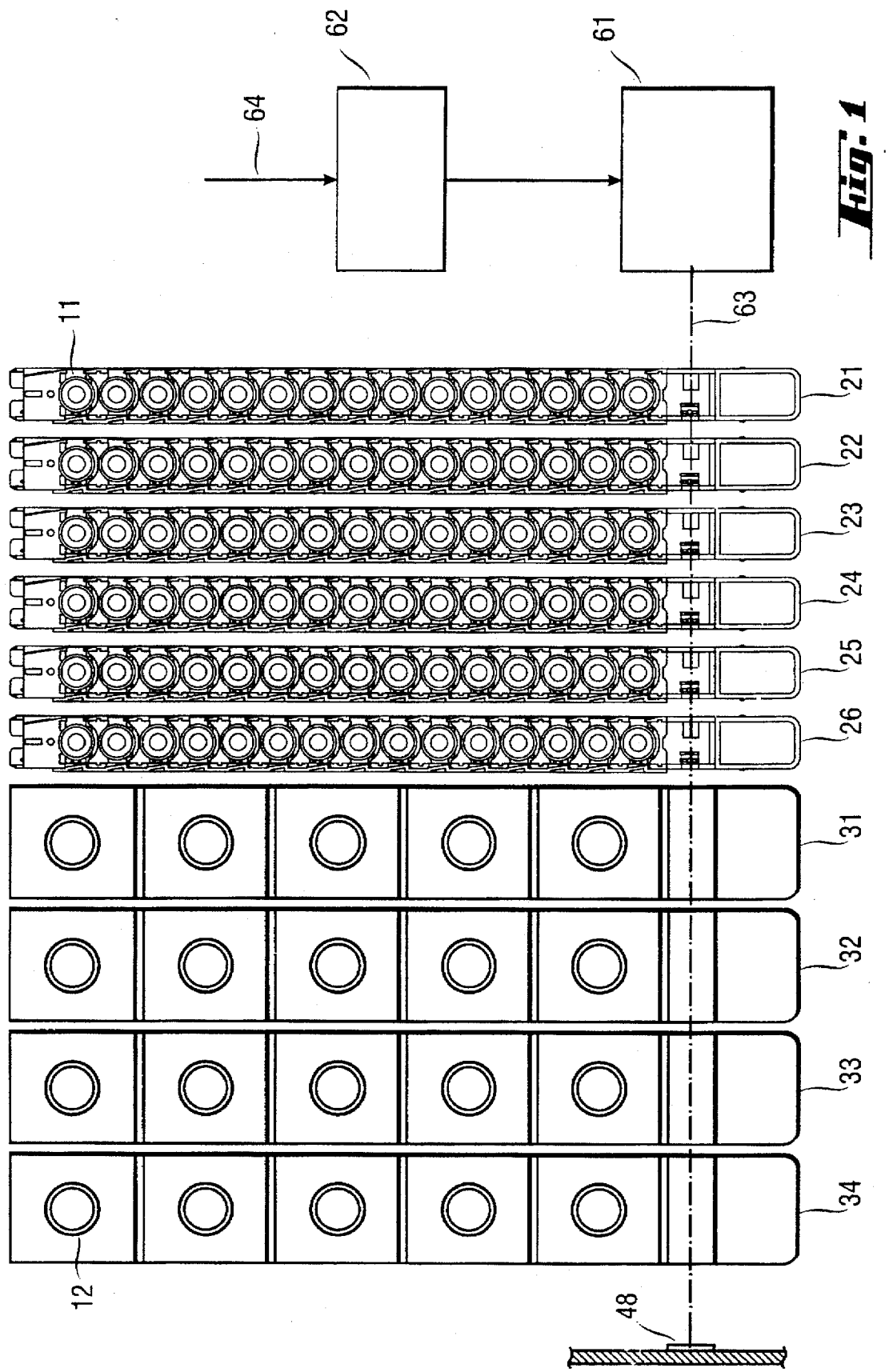
FIG. 1 is a diagrammatic plan view of the arrangement of vessel holders in an analyzer.

FIG. 1 is a plan view of an analyzer according to the invention for automatic analysis of liquid samples. As shown in FIG. 1, vessel holders 21 to 26 for sample vessels 11 and vessel holders 31 to 34 for reagent vessels 12 are disposed parallel to one another in an analyzer. A number of vessels of the same kind are disposed in each vessel holder, for example, vessels 11 holding samples are disposed in the vessel holder 21.

As shown in FIG. 1., a bar code reader 61 in the analyzer is permanently disposed on one side of the arrangement of vessel holders. The bar code reader 61 reads all the bar code labels on the vessel holders 21 to 26, 31 to 34 and on the vessels therein, the reading process occurring during insertion of each vessel holder into the analyzer. The path of the light beam used for reading the bar code labels is indicated by a dotted line 63. When the light beam does not strike a label on a vessel holder or vessel, it falls on a label 48 disposed on a fixed side wall of the analyzer outside the arrangement of vessel holders. The label 48 is read for the purpose of adjusting the bar code reader 61.

The analyzer in FIG. 1 also contains means for automatically adjusting the focal range of the bar code reader in dependence on the distance between the vessel holder and the bar code reader. This is done by means shown in FIG. 8 which detect the position of each vessel holder in the analyzer and generate corresponding electronic signals and thus, via a line 64 and a control circuit 62 shown in FIG. 1, suitably adjust the focal range of the bar code reader in dependence on the distance between the vessel holder and the bar code reader. In this manner the bar code reader can correctly read bar code labels at different distances from the bar code reader.

Figure 2:
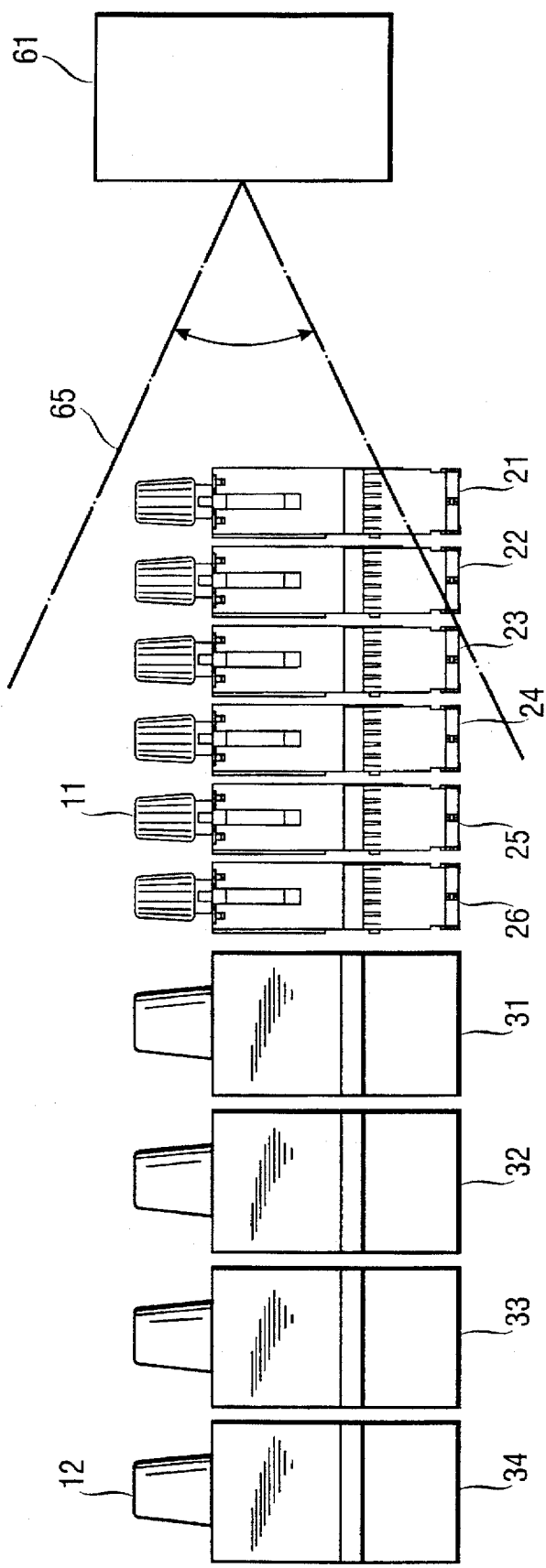
FIG. 2 is a diagrammatic front view of the arrangement in FIG. 1.

FIG. 2 diagrammatically shows the relative positioning of the vessel holders 21 to 26 and 31 to 34 and of the bar code reader 61 in the analyzer in FIG. 1. FIG. 2 shows the angle 65 scanned by the reading beam 63 during the reading process.

Figure 3:
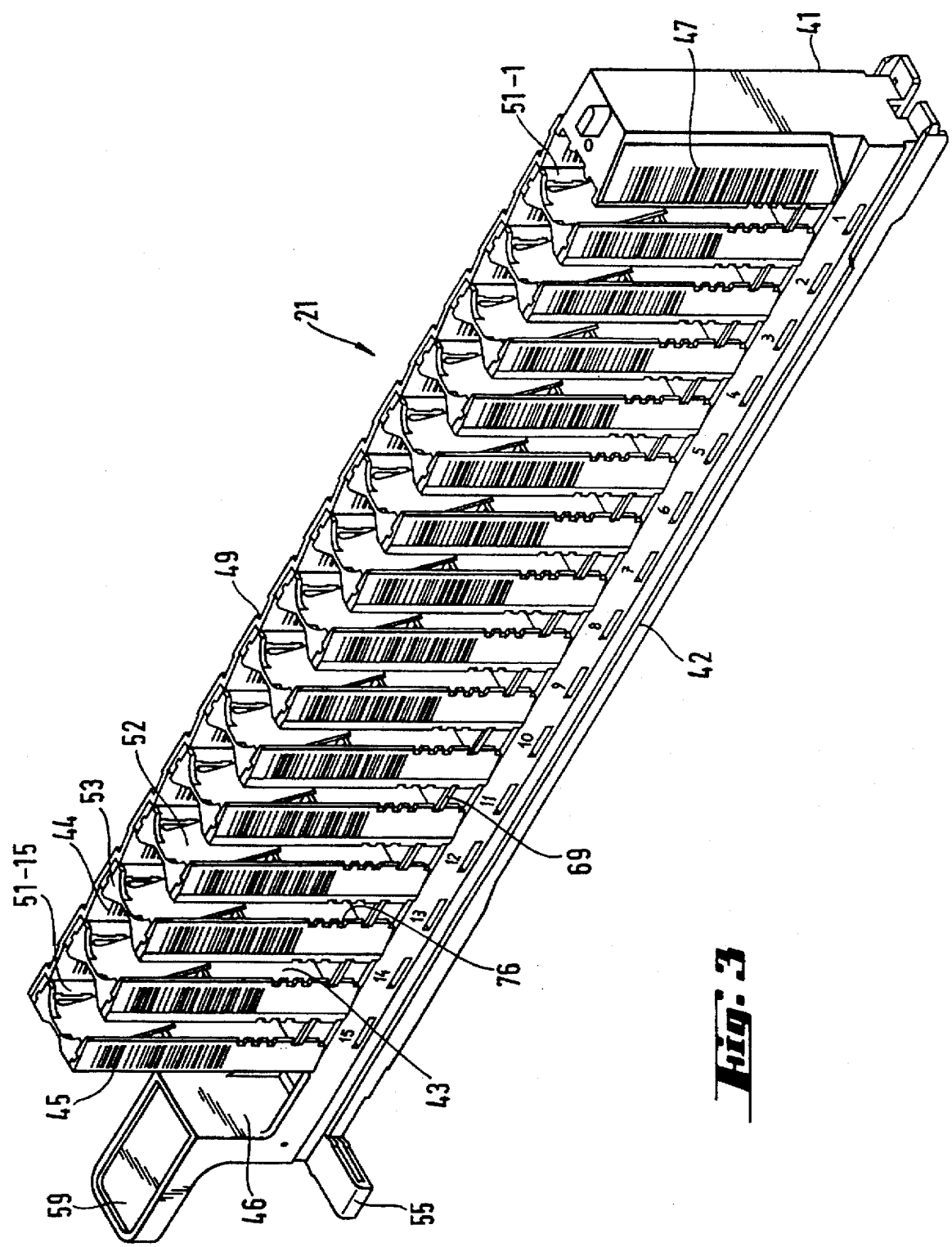
FIG. 3 is a perspective front view of one of the vessel holders 21–26 according to the invention shown in FIG. 1.

FIG. 3 is a perspective view of one of the vessel holders 21 to 26 for sample vessels 11 according to the invention and shown in FIG. 1, for example vessel holder 21. The vessel holder 21 has an elongate body 41 manufactured in one piece and containing a single straight row of identical elongate chambers 51-1 to 51-15 each for receiving a vessel 11. All these chambers have a common base 42, with respect to which they are perpendicularly disposed. Neighboring chambers, for example 51-1 and 51-2, are separated by a partition 43.

Each chamber 51-1 to 51-15 has a tongue 52 extending inwards from the top part of a partition 43 and serving as a spring for exactly positioning a vessel 11 in the chamber. The tongue 52 has a holder 53 for insertion into corresponding openings in the partition 43.

On the inner surface of a side wall 49, each chamber 51-1 to 51-15 bears a first bar code label 44 for detecting the absence of a vessel in the chamber. The outside of a side wall of each chamber 51-1 to 51-15 bears a second bar code label 45 for detecting the position of the chamber in the vessel holder. On the vessel holder delivered to the user, the bar code labels 44 and 45 of all chambers are stuck to the surfaces provided.

At a first end, the vessel holder 21 bears a bar code label 47 secured to the outside of a side wall adjacent the first chamber 51-1 of the vessel holder. The bar code label 47 is for detecting the number of the vessel holder 21. At its opposite end, the vessel holder 21 has a surface 59 disposed parallel to the base of the holder and used for receiving a label with the holder's number in the form of a figure. This label, like the label 47, is delivered separately from the vessel holder and applied by the user.

The first bar code label 44 and the second bar code label 45 of each chamber 51-1 to 51-15 and the bar code label 47 are read by the bar code reader 61 on the same side of the vessel holder when the holder is inserted into the analyzer.

Figure 4:
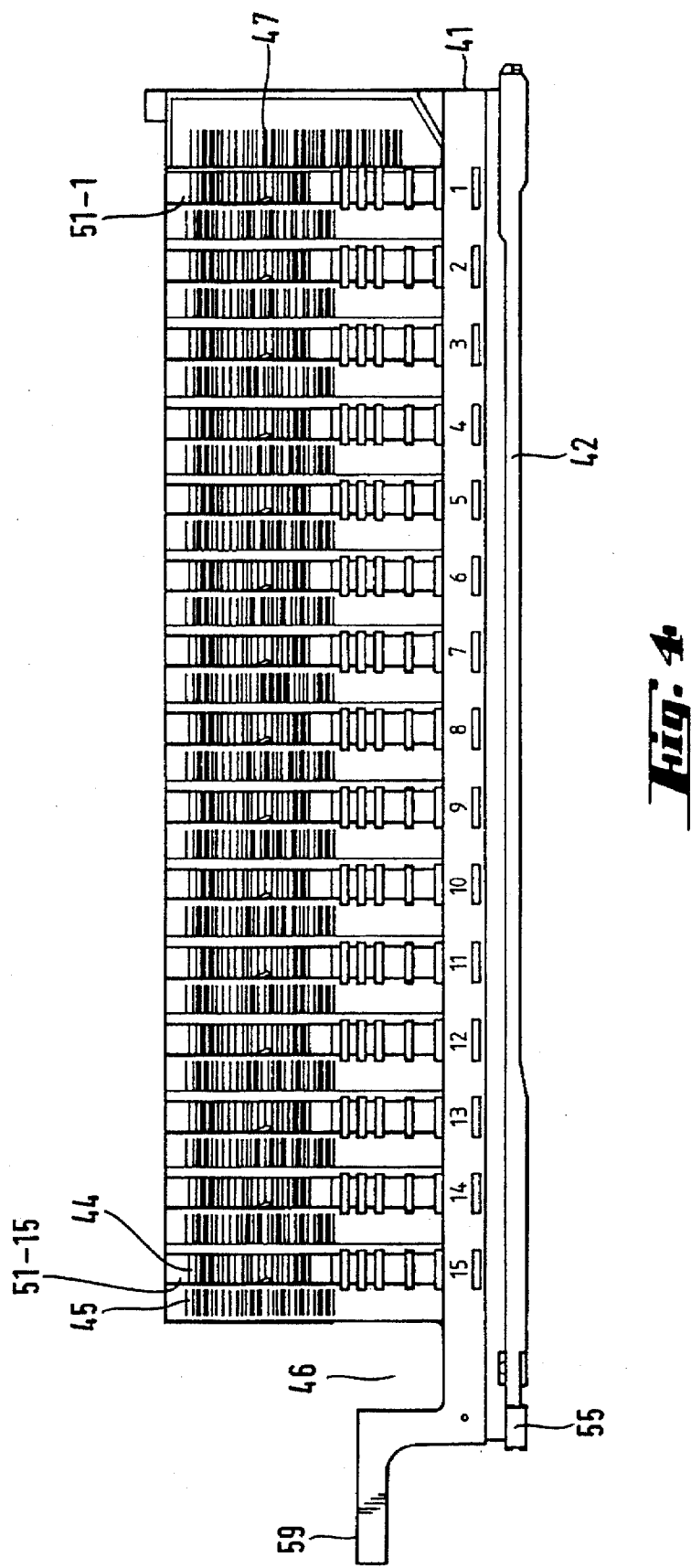
FIG. 4 is a front view of the vessel holder in FIG. 3.

FIG. 4 shows a front view of the vessel holder in FIG. 3. FIG. 4 shows all the bar code labels 44, 45 and 47 on the vessel holder and a window 46 through which the reading beam of the bar code reader 61 travels during the reading process.

Figure 5:
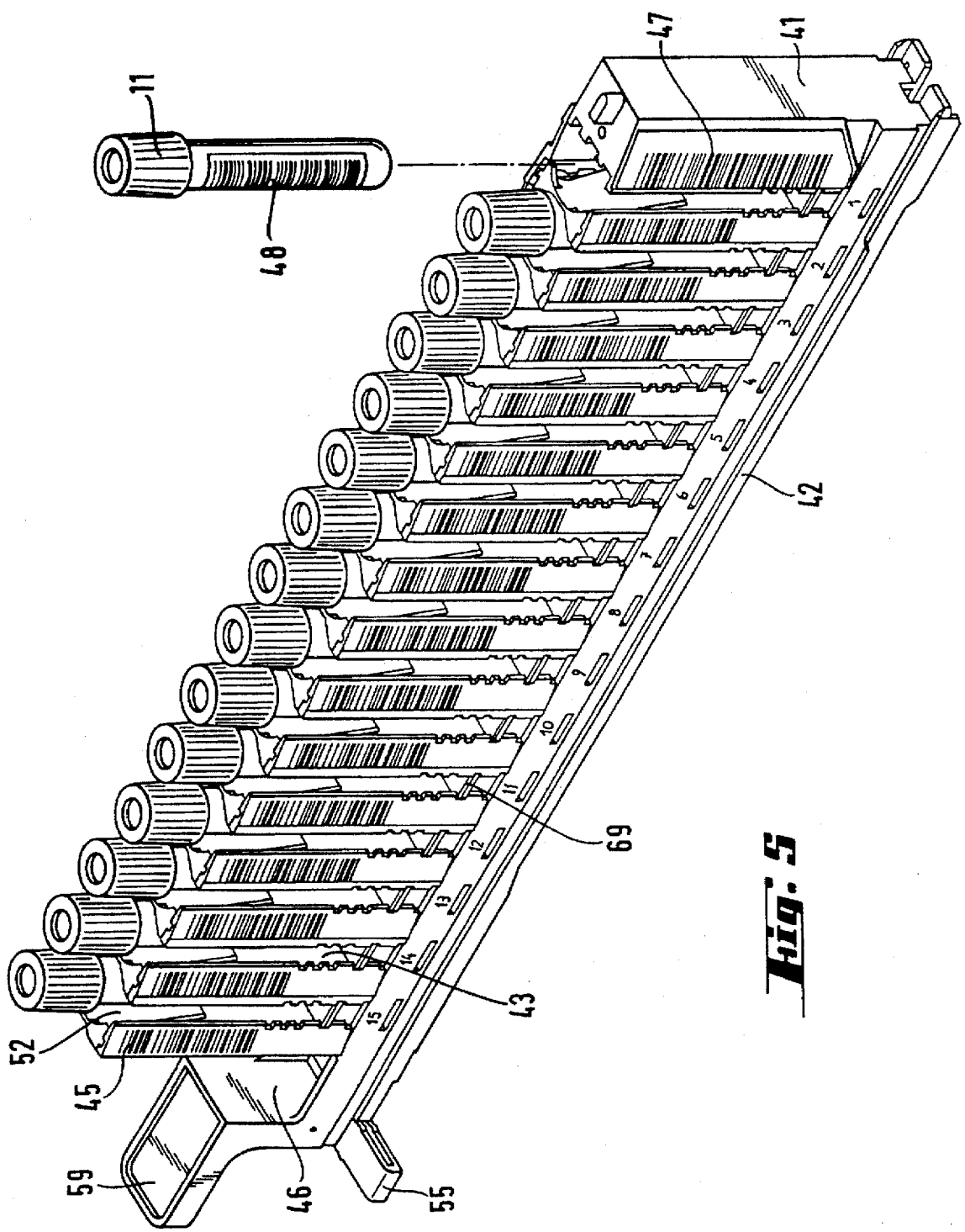
FIG. 5 is a perspective view of a vessel holder as in FIG. 3 in which the chambers 51-1 to 51-15 each contain a sample vessel 11.

FIG. 5 shows a vessel holder according to FIG. 3 in which the chambers 51-1 to 51-15 each contain a sample vessel 11. Each sample vessel also has a bar code label 48. Each sample vessel 11 is disposed in the vessel holder chamber so that the bar code label stuck to it can also be read by the bar code reader 61.

Figure 6:
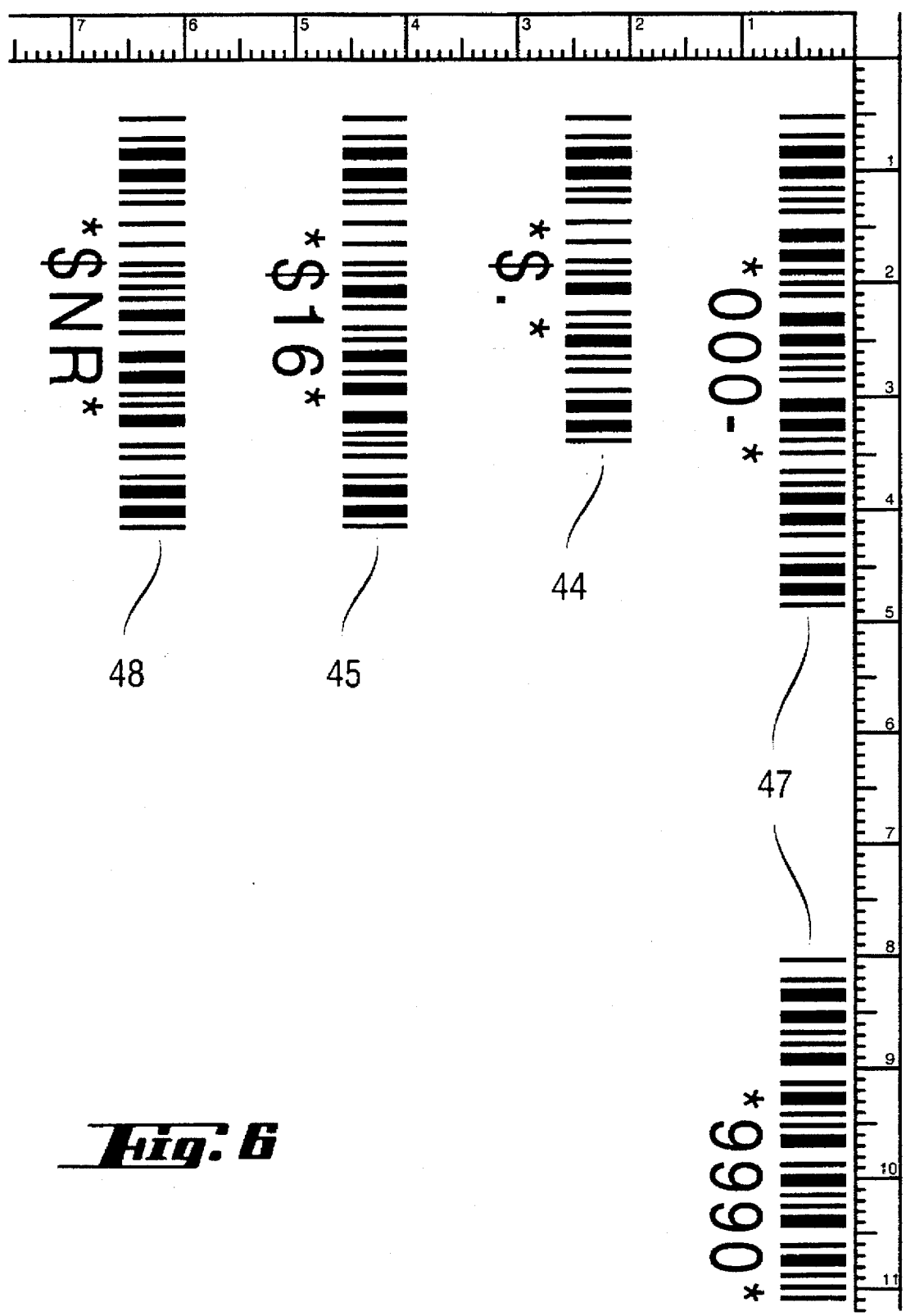
FIG. 6 gives views of samples of bar code labels 44, 45, 47 and 48.

FIG. 6 shows samples of bar code labels 44, 45, 47 and 48.

The above description of the vessel holders 21–26 for sample vessels substantially also applies to the vessel holders 31–34 for reagent vessels. The vessel holders 31–34 differ from the vessel holders 21–26 mainly in the number of chambers per vessel holder and in the dimensions of the chamber.

For simplicity, the vessel holders are shown in the drawings without the vessels which they contain during use in an analyzer.

Figure 7:
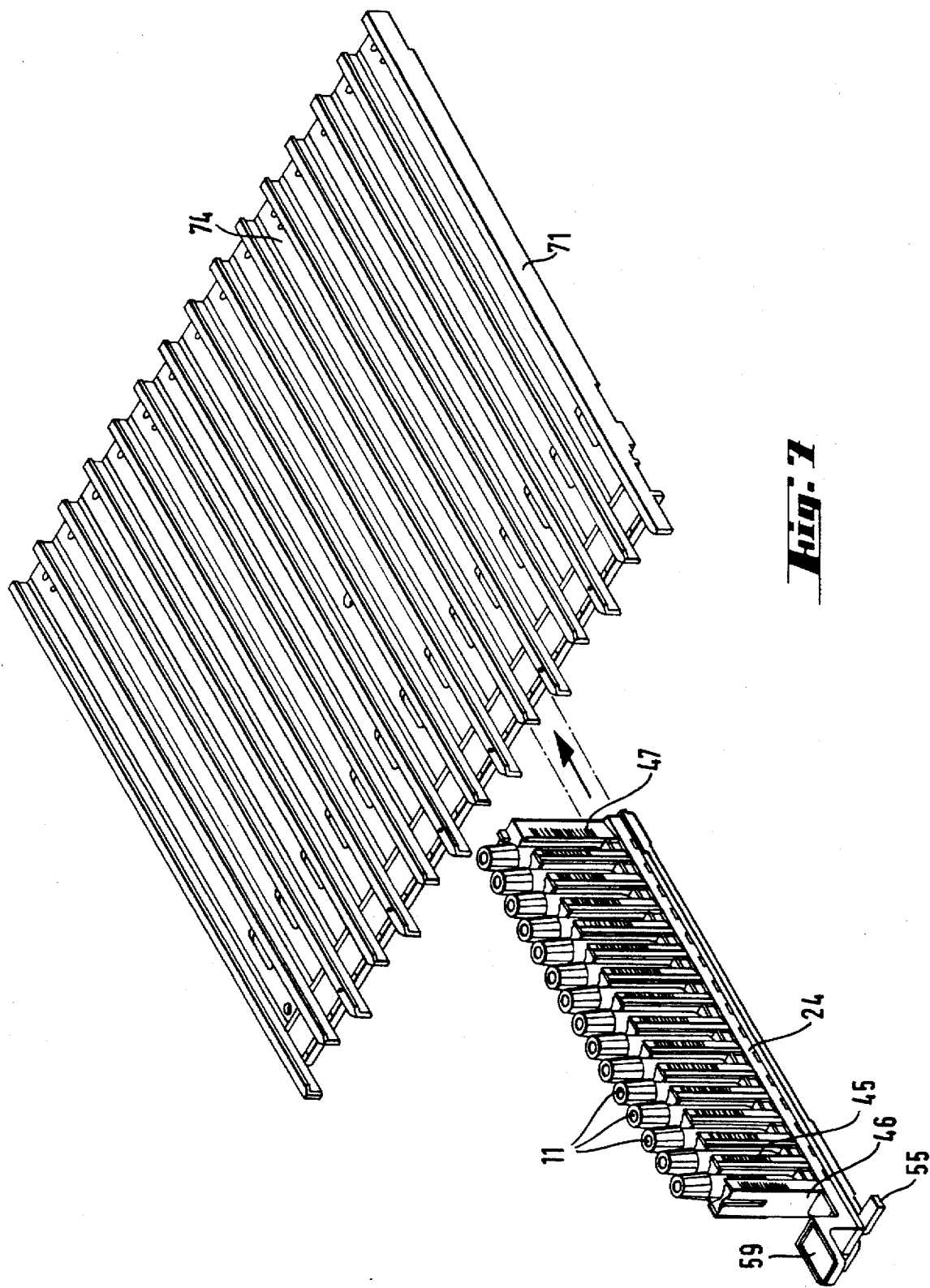
FIG. 7 is a perspective view of a carrier plate on which the vessel holders in FIG. 1 are arranged.

In the analyzer in FIG. 1, the vessel holders are disposed in corresponding tracks in a carrier plate (not shown in FIG. 1). As shown in FIG. 7, each vessel holder 24 is inserted into a free track 74 on a carrier plate 71. As shown in the exploded view in FIG. 8, an arrangement 81 of inductive sensors 82 and lifting magnets 83 is disposed under the carrier plate 71, one inductive sensor and one lifting magnet being provided for each track. When a vessel holder 24 approaches the path 74 of the carrier plate, the inductive sensor 82 underneath the track detects the approach of a metallic knob on the base and near the tip of the vessel holder 24. In this manner the position of the vessel holder is detected, generating a corresponding electric signal which is supplied to the control circuit 62 (in FIG. 1).

Figure 8:
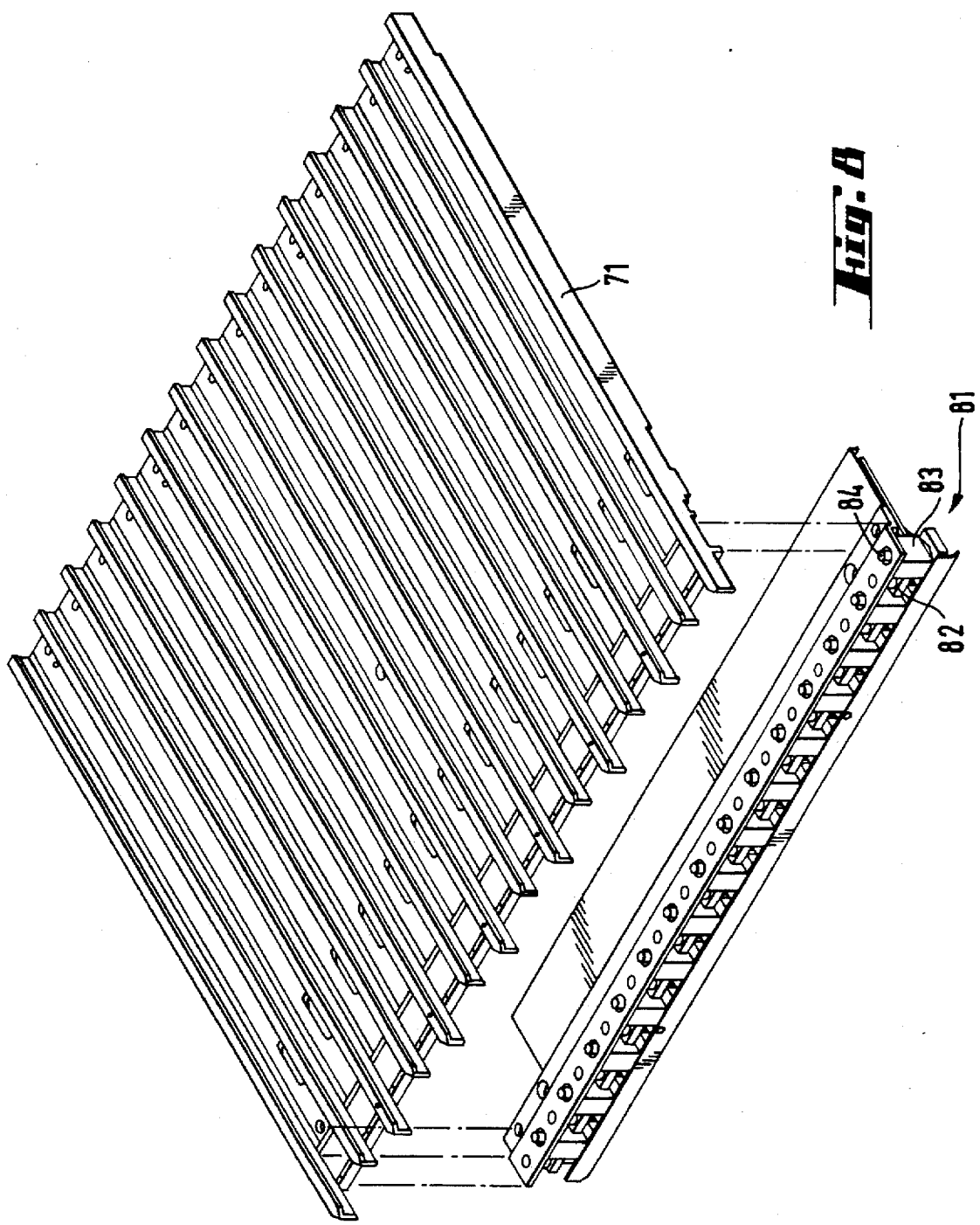
FIG. 8 is a perspective view of the carrier plate 71 in FIG. 7 and of an arrangement of inductive sensors and lifting magnets disposed immediately under the front part of the carrier plate 71.

The arrangement of lifting magnets 83 and associated pins 84 shown in FIG. 8 is used for selectively opening or closing the access of a vessel holder to each track on the carrier plate 71. Access to a given track is blocked by a pin 84 movable by the lifting magnet, when the corresponding lifting magnet 83 is in a first state. By suitable actuation of the lifting magnet, the pin 84 can be pulled out, thus giving the vessel holder 24 access to the track.

Manual insertion of a vessel holder 24 into a free track 74 on the carrier plate 71 as in FIGS. 5 and 6 will now be described with reference to FIGS. 9 and 10.

Figure 9:
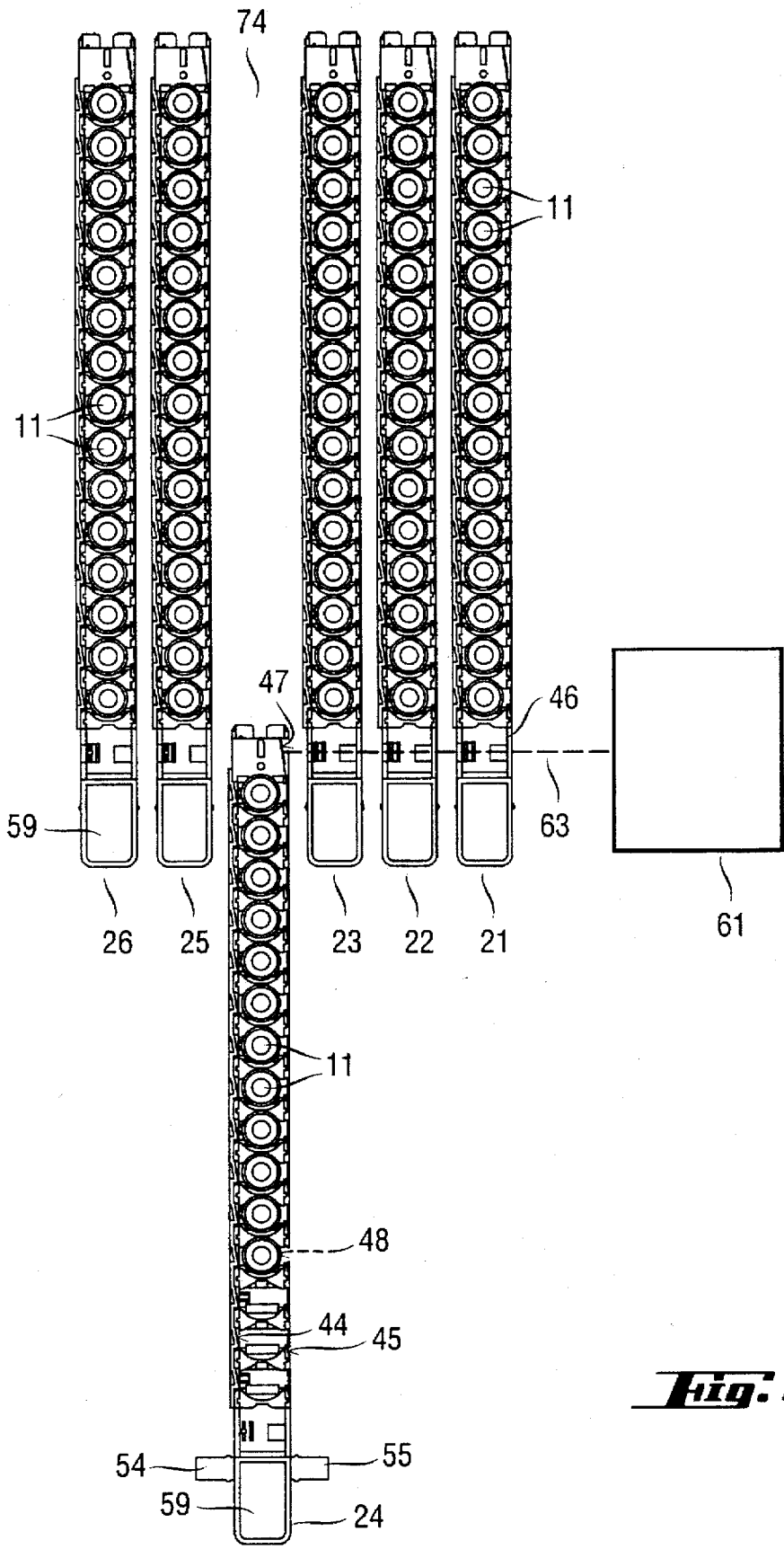
FIG. 9 is a diagrammatic plan view of an arrangement of vessel holders immediately before insertion of a vessel holder into a free space.

In FIG. 9 the free track 74 is between the tracks occupied by vessel holders 25 and 23. When the vessel holder 24 is inserted into the track 74, the tip of the vessel holder 24 first strikes against the pin 84 of the lifting magnet 83 projecting through an opening in track 74. When this occurs, the vessel holder 24 is in the position shown in FIG. 9. In this position the bar code label 47 bearing the identification number of the vessel holder 24 is read by the bar code reader 61. The light beam 63 travels through the window 46 of the vessel holders 21 to 23. After this reading process, the bar code reader 61 delivers a control signal which activates the lifting magnet 83, thus withdrawing the pin 84 and enabling the vessel holder 24 to be inserted into the track 74.

Figure 10:
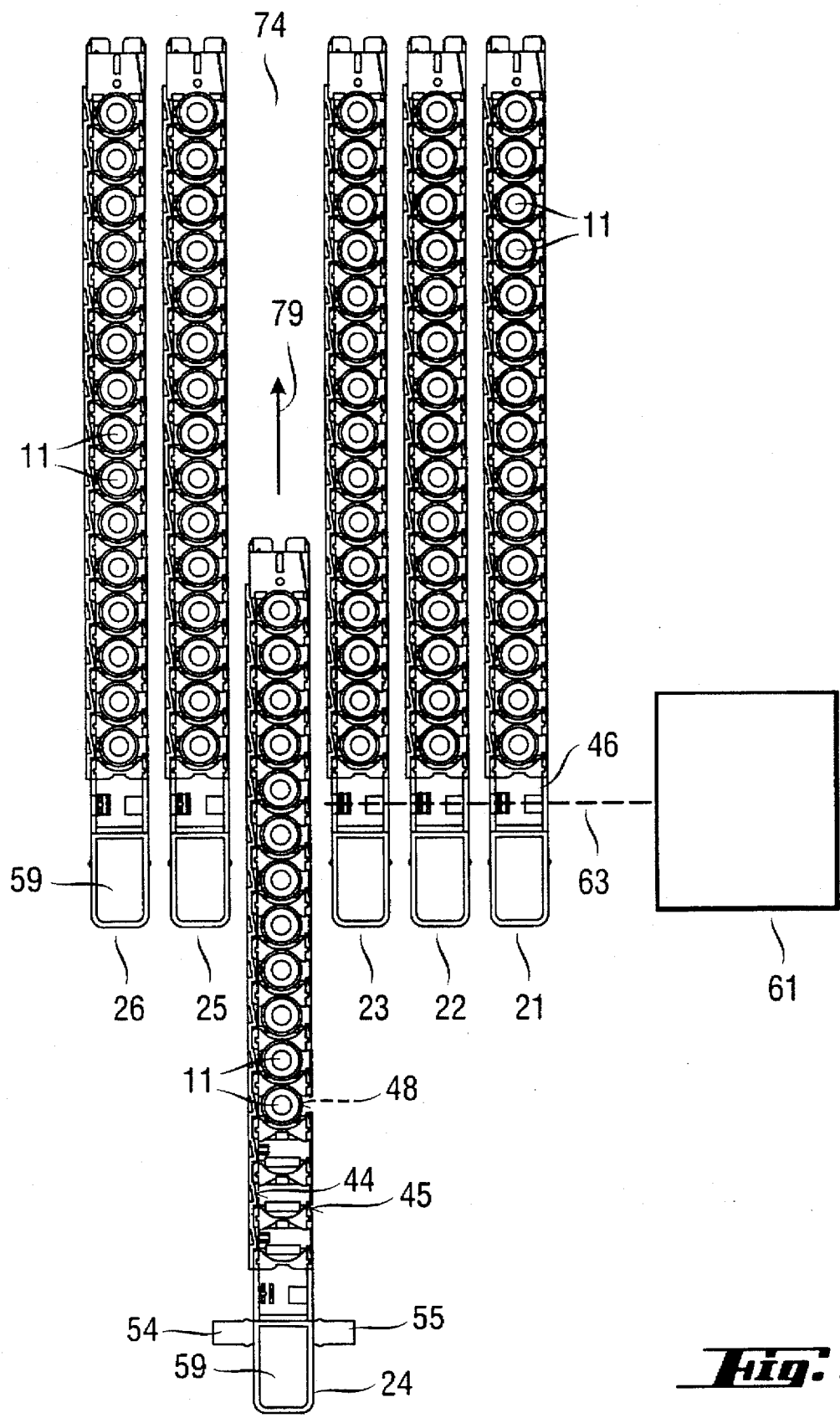
FIG. 10 is a diagrammatic plan view of an arrangement of vessel holders during insertion of a vessel holder into a free space.

The movement of the vessel holder 24 during manual insertion into the track 74 is indicated by arrow 79 in FIG. 10. During this movement, the bar code labels 45 on all chambers 51-1 to 51-15 and the bar code labels 48 on the sample vessels in these chambers are read by the bar code reader 61. When a chamber does not contain a sample vessel, the bar code label 44 of the chamber is read and indicates that the chamber is empty. When all bar code labels have been correctly read, the bar code reader 61 delivers a control signal which communicates corresponding information to the central control means of the analyzer. If on the other hand one of the bar code labels cannot be correctly read, no such message is given and the user is requested by a suitable signal to re-insert the vessel holder 24 so that the reading process can be repeated.

When the vessel holder 24 has occupied its predetermined position in the track 74, this is detected by the inductive sensor 82, which senses a second metallic head at one end of the base of the vessel holder 24. As a result of this detection process, the track 74 is locked by the corresponding lifting magnet 83 and the corresponding pin 84, so that the vessel holder 24 is retained in this track until the track 74 has been unlocked by a corresponding control signal generated by the central control means of the analyzer when the samples have been completely processed in the vessel holder 24.

The scanning frequency of the bar code reader is made sufficiently high for all bar code labels on a vessel holder to be correctly read during manual insertion of the holder into the analyzer. Determining appropriate scanning frequency and other parameters, such as scanning angle, is within the knowledge of a skilled artisan.

The above description of the process of inserting the vessel holder 24 into a corresponding track on the carrier plate 71 and the process of reading the bar code labels by the reader 61 also applies to the other vessel holders and vessels in the analyzer in FIG. 1.

Other details of the vessel holder in FIG. 3 will now be described with reference to FIGS. 11–16.

Figure 11:
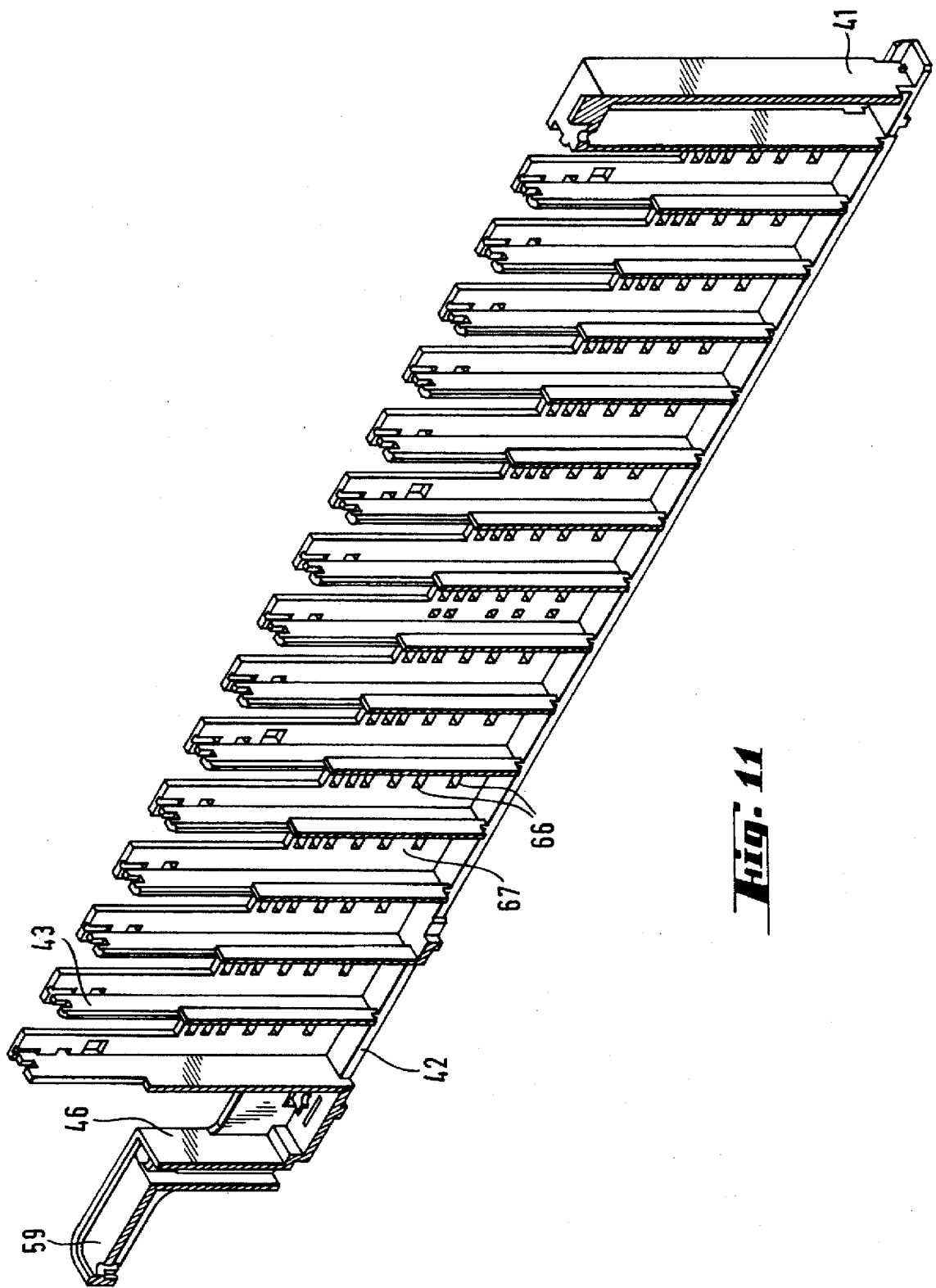
FIG. 11 is a perspective sectional view of a vessel-holder as in FIG. 3.

The sectional view in FIG. 11 more particularly shows the common base 42 of the chambers 51-1 to 51-15 and the partitions between neighboring chambers.

Figure 12:
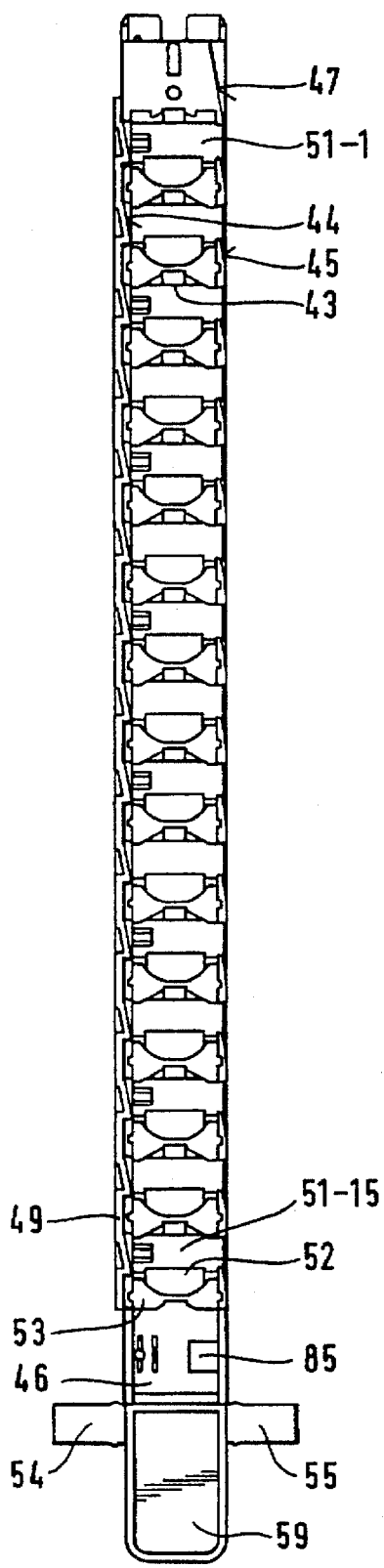
FIG. 12 is a plan view of the vessel holder in FIG. 3.

FIG. 12 is a plan view of the vessel holder in FIG. 3. As FIG. 11 shows, the inner surface bearing the first bar code label 44 and the outer surface bearing the second bar code label 45 are disposed in the same way relative to a plane defined by the longitudinal axis of the vessel holder and the longitudinal axis of one chamber. In a preferred embodiment of the vessel holder, the said inner surface and outer surface are parallel to one another and at an angle of about 10° to the plane defined by the longitudinal axis of the holder and the longitudinal axis of one chamber.

In a preferred embodiment of the vessel holder, also, the inner surface bearing the first bar code label 44 is a part of the inner surface of a common side wall 49 of all chambers 51-1 to 51-15, the side wall 49 being separably connected to the body of the holder.

Figure 13:
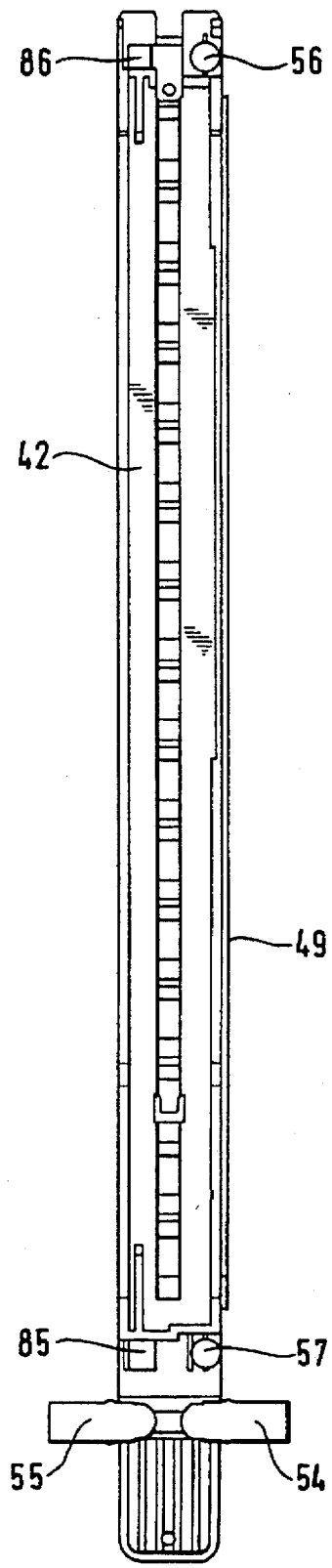
FIG. 13 is a bottom view of the vessel holder in FIG. 3.

FIG. 13 is a bottom view of the vessel holder in FIG. 3.

FIG. 14 is a left side view and FIG. 15 is a right side view of the vessel holder in FIG. 3.

As shown in FIGS. 12 to 14, the vessel holder in FIG. 3 has flat supports 54, 55 at one end, the lower surface of the supports being coplanar with the lower surface of the vessel holder base 42. Each support 54, 55 is held in a lateral position by a torsion spring. When the vessel holder is inserted into the analyzer, the supports 54 and 55 are folded against the force of the torsion spring and occupy a position parallel to the longitudinal axis of the vessel holder. The supports 54 and 55 give the vessel holder increased stability against tipping, such as if the vessel holder is placed on a table before insertion into the analyzer.

As shown in FIG. 13, in a preferred embodiment of the vessel holder in FIG. 3 metallic knobs 56, 57 are secured to the base 42 and are detectable by an inductive sensor.

As shown in FIG. 13, in a preferred embodiment of the vessel holder in FIG. 3, openings 85 and 86 are present in the base 42, for securing the vessel holder on the carrier plate 71.

Figure 16:
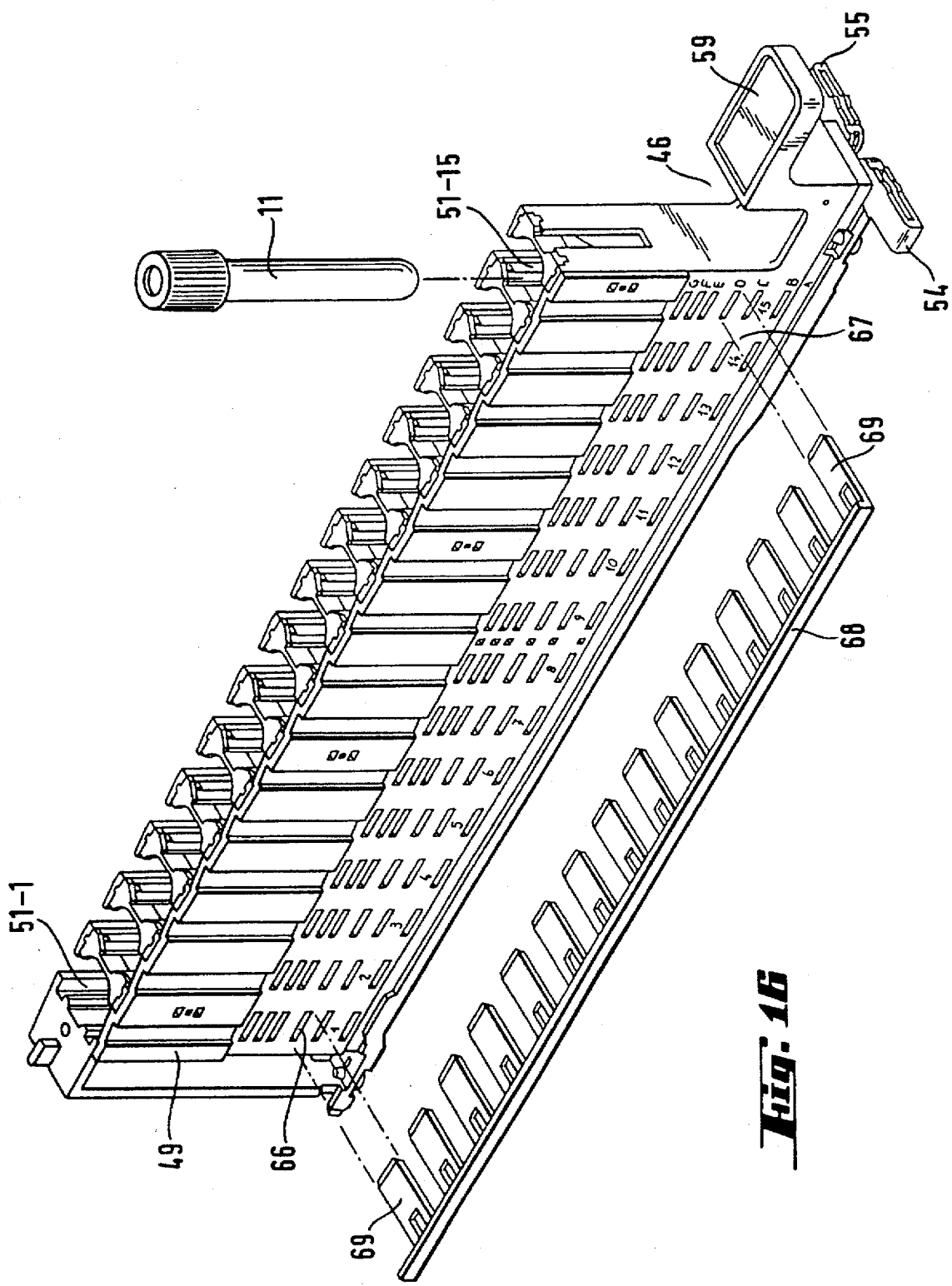
FIG. 16 is a perspective rear view of one of the vessel holders 21–26 according to the invention shown in FIG. 1.

FIG. 16 is a perspective back view of the vessel holder in FIG. 3.

As shown in FIG. 16, a side wall 67 common to all chambers 51-1 to 51-15 has horizontal rows of slot-like openings 66 at various vertical positions relative to the base of the holder. Flat intermediate bases 69 supported like a comb by a strip 68 can be inserted through the slot openings. This is a means of adapting the depth of chambers 51-1 to 51-15 to the length of the vessels 11 used. In a preferred embodiment the tip of each intermediate base 69 is disposed in a corresponding opening 76 in the side wall of the chamber opposite the side wall 67.

Upon reading the present specification, various alternative embodiments will become obvious to the skilled artisan. For example, within the scope of the invention each of the above mentioned bar code labels can be replaced by equivalent means, such as by an imprint stamped on a surface of the vessel holder. These variations are to be considered within the scope and spirit of the present invention, which is only to be limited by the claims which follow and their equivalents.

What is claimed is:

1. An analyzer for automatically performing analytical operations using liquid samples and reagents contained in vessels, the analyzer comprising:

a) at least two vessel holders that during operation of the analyzer are disposed parallel to one another and located at predetermined positions in the analyzer, each vessel holder being configured and dimensioned to hold a plurality of vessels, each vessel holder containing a single straight row of parallelly oriented elongate chambers which are located at predetermined positions within the vessel holder, each chamber being configured and dimensioned for receiving one vessel that within the chamber can either be present or absent, adjacent chambers being separated by a partition, each chamber having a first side wall and a second side wall positioned and dimensioned so that the first side wall and the second side wall in cooperation with the partitions form the sides of the chamber, each side wall having an inner surface and an outer surface, the inner surface of the first side wall of each chamber bearing a first bar code label for detecting the absence of a vessel in the chamber, and the outer surface of the second side wall of each chamber bearing a second bar code label for detecting the position of the chamber in the vessel holder, the first bar code label and the second bar code label being readable from the side of the vessel holder formed by the second side walls;

b) a bar code reader having a focal range, the bar code reader being fixedly disposed in the analyzer and positioned at a distance from each vessel holder to read all of the bar code labels on each vessel holder as the vessel holder is inserted into the analyzer; and c) means for automatically adjusting the focal range of the bar code reader in dependence on the distance between the bar code reader and the vessel holder.

2. The analyzer according to claim 1, wherein the means for automatically adjusting the focal range of the bar code reader contains means for detecting the position of a vessel holder in the analyzer.

3. The analyzer according to claim 1, wherein the bar code reader has a scanning frequency that permits correct reading of all bar code labels on a vessel holder during manual insertion of the vessel holder into the analyzer.

4. The analyzer according to claim 1, wherein the at least two vessel holders comprise a first vessel holder and a second vessel holder and at least the second vessel holder contains a window through which light can traverse to reach the first vessel holder.

5. The analyzer according to claim 4, wherein the bar code reader is designed to read each bar code label on the first vessel holder using a light beam which travels through the window in the second vessel holder when the second vessel holder is disposed in the analyzer between the first vessel holder and the bar code reader.

6. The analyzer according to claim 1 further comprising means for securing the vessel holder in the analyzer during operation of the analyzer.

* * * * *